(12) United States Patent
Wright et al.

(10) Patent No.: US 12,161,607 B2
(45) Date of Patent: *Dec. 10, 2024

(54) COMBINATION OF CANNABINOIDS IN THE TREATMENT OF LEUKEMIA

(71) Applicant: Jazz Pharmaceuticals Research UK Limited, Sittingbourne (GB)

(72) Inventors: Stephen Wright, Cambridge (GB); Wai Liu, London (GB); Katherine Scott, London (GB); Angus Dalgleish, London (GB)

(73) Assignee: Jazz Pharmaceuticals Research UK Limited, Sittingbourne (GB)

( * ) Notice: Subject to any disclaimer, the term of this patent is extended or adjusted under 35 U.S.C. 154(b) by 781 days.

This patent is subject to a terminal disclaimer.

(21) Appl. No.: 17/231,625

(22) Filed: Apr. 15, 2021

(65) Prior Publication Data

US 2021/0308072 A1   Oct. 7, 2021

Related U.S. Application Data

(63) Continuation of application No. 16/488,821, filed as application No. PCT/GB2018/050421 on Feb. 16, 2018, now Pat. No. 11,000,486.

(30) Foreign Application Priority Data

Feb. 27, 2017 (GB) .................................... 1703115

(51) Int. Cl.
| | | |
|---|---|---|
| *A61K 31/05* | (2006.01) | |
| *A61K 31/352* | (2006.01) | |
| *A61K 31/475* | (2006.01) | |
| *A61K 31/7068* | (2006.01) | |
| *A61P 35/02* | (2006.01) | |

(52) U.S. Cl.
CPC ............ *A61K 31/05* (2013.01); *A61K 31/352* (2013.01); *A61P 35/02* (2018.01); *A61K 31/475* (2013.01); *A61K 31/7068* (2013.01)

(58) Field of Classification Search
CPC ........ A61K 31/05; A61K 31/352; A61P 35/02
See application file for complete search history.

(56) References Cited

U.S. PATENT DOCUMENTS

| | | |
|---|---|---|
| 6,403,126 B1 | 6/2002 | Webster |
| 6,949,582 B1 | 9/2005 | Wallace |
| 8,293,786 B2 | 10/2012 | Stinchcomb |
| 8,632,825 B2 | 1/2014 | Diez et al. |
| 8,673,368 B2 | 3/2014 | Guy et al. |
| 8,790,719 B2 | 7/2014 | Parolaro et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Whalley et al. |
| 9,259,449 B2 | 2/2016 | Raderman |
| 9,522,123 B2 | 2/2016 | Whalley et al. |
| 9,474,726 B2 | 10/2016 | Guy et al. |
| 9,675,654 B2 | 6/2017 | Parolaro et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,856,184 B2 | 5/2018 | Guy et al. |
| 9,956,183 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |
| 10,111,840 B2 | 10/2018 | Guy et al. |
| 10,137,095 B2 | 11/2018 | Guy et al. |
| 10,220,005 B2 | 3/2019 | Martinez-Orgado |
| 10,226,433 B2 | 3/2019 | DiMarzo et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

Wiley et al., "Cytosine arabinoside transport and metabolism in acute leukemias and T cell lymphoblastic lymphoma", Journal of Clinical Investigation, vol. 75, No. 2, pp. 632-642 (1985).*
GB 1703115.4, Dec. 8, 2017, *Combined Search Report and Examinaiton Report.
PCT/GB2018/050421, Apr. 20, 2018, *International Search Report and Written Opinion.
PCT/GB2018/050421, Sep. 6, 2019, * International Preliminary Report on Patentability.
[No Author Listed] Database WPI Week 201252. Clarivate Analytics. Accession No. 2012-J67237. Jan. 8, 2011. 2 pages.
Gallily et al., Gamma-irradiation enhances apoptosis induced by cannabidiol, a non-psychotropic cannabinoid, in cultured HL-60 myeloblastic leukemia cells. Leuk Lymphoma. Oct. 2003;44(10):1767-73.

(Continued)

*Primary Examiner* — Kevin E Weddington
(74) *Attorney, Agent, or Firm* — Cooley LLP

(57) ABSTRACT

The present invention relates to the use of a combination of two different cannabinoids in the treatment of leukaemia. The combination of CBD with THC appears to be particularly effective in reducing cell number in this disease. Preferably the cannabinoids are used in the form of an extract of *Cannabis* such that many of the naturally occurring compounds are co-extracted with the THC or CBD. Alternatively, the cannabinoids are present in the form of a highly purified extract of *Cannabis*, wherein the CBD or THC are present at greater than 98% of the total extract (w/w) and the other components of the extract are characterized. Alternatively, the CBD and THC may be synthetically produced. A specific ratio of CBD and THC such as 10:1 to 1:10 (CBD:THC) or more preferably between 2:1 to 1:2 (CBD:THC) may be used.

16 Claims, 4 Drawing Sheets

(56) References Cited

U.S. PATENT DOCUMENTS

| | | |
|---|---|---|
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,729,665 B2 | 8/2020 | Whalley et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,000,486 B2 * | 5/2021 | Wright et al. ....... A61K 31/352 |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Wright et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 | 5/2022 | Whalley et al. |
| 11,357,741 B2 | 6/2022 | Guy et al. |
| 11,400,055 B2 | 8/2022 | Guy et al. |
| 11,406,623 B2 | 8/2022 | Guy et al. |
| 11,413,266 B2 | 8/2022 | Biro et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 2004/0110828 A1 | 6/2004 | Chowdury et al. |
| 2005/0266108 A1 | 12/2005 | Flockhart et al. |
| 2006/0039959 A1 | 2/2006 | Wessling |
| 2007/0060638 A1 | 3/2007 | Olmstead |
| 2008/0119544 A1 | 5/2008 | Guy et al. |
| 2008/0188461 A1 | 8/2008 | Guan |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0270845 A1 | 10/2012 | Bannister et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0167583 A1 | 6/2019 | Shah et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0069333 A1 | 3/2021 | Velasco Diez et al. |
| 2021/0100755 A1 | 4/2021 | Whalley et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Guy et al. |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0378715 A1 | 12/2022 | Guy et al. |
| 2022/0378738 A1 | 12/2022 | Guy et al. |
| 2022/0387347 A1 | 12/2022 | Whalley et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy et al. |
| 2023/0263744 A1 | 8/2023 | Guy et al. |

(56) References Cited

U.S. PATENT DOCUMENTS

| | | |
|---|---|---|
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig et al. |
| 2023/0372367 A1 | 11/2023 | Checketts et al. |
| 2023/0372368 A1 | 11/2023 | Checketts et al. |
| 2024/0016819 A1 | 1/2024 | Craig et al. |
| 2024/0025858 A1 | 1/2024 | Silcock et al. |
| 2024/0033229 A1 | 2/2024 | Guy et al. |
| 2024/0033272 A1 | 2/2024 | Checketts et al. |
| 2024/0043388 A1 | 2/2024 | Silcock et al. |
| 2024/0050452 A1 | 2/2024 | Craig et al. |
| 2024/0091241 A1 | 4/2024 | Guy et al. |

FOREIGN PATENT DOCUMENTS

| | | |
|---|---|---|
| CN | 101040855 A | 9/2007 |
| DE | 10 2012 105 063 A1 | 12/2013 |
| EP | 2 448 637 B1 | 5/2012 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2471565 A | 7/2012 |
| GB | 2478072 B | 12/2012 |
| GB | 2478074 B | 12/2012 |
| GB | 2492487 A | 1/2013 |
| KR | 20120080675 A | 7/2012 |
| WO | WO 2002/064109 A2 | 8/2002 |
| WO | WO 2003/099302 A1 | 12/2003 |
| WO | WO 2004/016246 A1 | 2/2004 |
| WO | WO 2004/016277 A2 | 2/2004 |
| WO | WO 2006/054057 A2 | 5/2006 |
| WO | WO 2006/133941 A2 | 12/2006 |
| WO | WO 2007/083098 A1 | 7/2007 |
| WO | WO 2007/138322 A1 | 12/2007 |
| WO | WO 2008/019146 A2 | 2/2008 |
| WO | WO 2008/094181 A2 | 8/2008 |
| WO | WO 2008/129258 A1 | 10/2008 |
| WO | WO 2008/144475 A1 | 11/2008 |
| WO | WO 2008/021394 A2 | 12/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 12/2009 |
| WO | WO 2011/001169 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/032351 A1 | 3/2013 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/059405 A1 | 4/2016 |
| WO | WO 2016/084075 A1 | 6/2016 |
| WO | WO 2016/087649 A2 | 6/2016 |
| WO | WO 2016/118391 A1 | 7/2016 |
| WO | WO 2016/147186 A1 | 9/2016 |
| WO | WO 2016/022936 A1 | 11/2016 |
| WO | WO 2016/199148 A1 | 12/2016 |
| WO | WO 2017/168138 A1 | 10/2017 |
| WO | WO 2018/002636 A1 | 1/2018 |
| WO | WO 2018/002637 A1 | 1/2018 |
| WO | WO 2018/037203 A1 | 3/2018 |

OTHER PUBLICATIONS

Kampa-Schittenhelm et al., Epigenetic hypomethylation of the 5'UTR of NADPH oxidase 4 (NOX4) by cannabidiol (CBD) results in increased protein expression, catalyzation of reactive oxygen species (ROS) and induction of apoptosis in acute leukemia. Oncol. Res. Treat. 2017;40(suppl 3):22. Abstract.

Liu et al., Enhancing the in vitro cytotoxic activity of Delta9-tetrahydrocannabinol in leukemic cells through a combinatorial approach. Leuk Lymphoma. Sep. 2008;49(9):1800-9. doi: 10.1080/10428190802239188.

Scott et al., Anticancer effects of phytocannabinoids used with chemotherapy in leukaemia cells can be improved by altering the sequence of their administration. Int J Oncol. Jul. 2017;51(1):369-377. doi: 10.3892/ijo.2017.4022. Epub May 29, 2017.

Scott et al., Enhancing the activity of cannabidiol and other cannabinoids in vitro through modifications to drug combinations and treatment schedules. Anticancer Res. Oct. 2013;33(10):4373-80.

Singh et al., Cannabis extract treatment for terminal acute lymphoblastic leukemia with a Philadelphia chromosome mutation. Case Rep Oncol. Sep.-Dec. 2013; 6(3): 585-592. EPub Nov. 28, 2013. doi: 10.1159/000356446.

Velasco et al., Anticancer mechanisms of cannabinoids. Curr Oncol. Mar. 2016; 23(Suppl 2):S23-S32. EPub Mar. 16, 2016. doi: 10.3747/co.23.3080.

[Author Unknown], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.

[Author Unknown], GW Pharmaceuticals Receives Orphan Drug Designation by FDA for Epidiolex® in the treatment of Lennox-Gastaut Syndrome, GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.

[Author Unknown], GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, https://www.gwpharm.com/about-us/news/gw-pharmaceuticals-announces-preliminary-resutls-phase-2a-study-its-pipeline-compound, 5 pages.

[Author Unknown], "What are the Highest CBD Strains?" Oct. 15, 2014, retrieved on Feb. 16, 2017, URL www.leafscience.com/2014/10/15/highest-cbd-strains/, 2 pages.

[Author Unknown], Cannabinoid. Wikipedia. Retrieved Mar. 1, 2017 from https://en.wikipedia.org/wiki/Cannabinoid, 15 pages.

[Author Unknown], GW Pharmaceuticals Announces Epidiolex(R) Receives Fast Track Designation from FDA for the Treatment of Dravet Syndrome, GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment, 2 pages.

[Author Unknown], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.

(56) References Cited

OTHER PUBLICATIONS

[Author Unkown], "Orphan Drug Designation Granted for Epidiolex in Dravet syndrome by the FDA-Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
[Author Unkown], Missouri House passes cannabis extract legislation, Kansas City Star, 2014, https://kansascity.com/news/politics-government/article346747.html, 2 pages.
[Author Unknown], "Convulsive Disorders and Their Interference with Driving," Medicos., retrieved Feb. 10, 2017. Retrieved from the Internet: URL <https://www.medicosporlaseguridadvial.com/en/clinical-subjects/neurologic-diseases/convulsive-disorders-and-their-interference-with-driving/>, 2014, 3 pages.
[Author Unknown], Cover and Table of Contents, J Pharmacology and Exp. Therapeutics, Feb. 2020, 332(2), 4 pages.
Alger, "Not too excited? Thank your endocannabinoids," Neuron, 51(4):393-395 (2006).
American Epilepsy Society, Three Studies Shed New Light on the Effectiveness of Cannabis in Epilepsy, Oct. 14, 2014, 2 pages.
Ames et al., "Anticonvulsant effect of cannabidiol," S Afr Med J., Jan. 4, 1986; 69(1):14, 1 page.
Arain, "Pregabalin in the management of partial epilepsy," Neuropsychiatr Dis Treat., 407-13 (2009).
Arslan et al., "Self-emulsifying drug delivery systems," FABAD J Pharma Sci, 38:55-64 (2013).
Arimanoglou et al., "All children who experience epileptic falls do not necessarily have Lennox-Gastaut syndrome . . . but many do," Epileptic Discord, 13: S3-S13 (2011).
Avoli et al. "Cellular and molecular mechanisms of epilepsy in the human brain," Prog Neurobiol., 77(3):166-200 (2005).
Bakhsh, "Key Attributes of TKDL," Miftaah-al-Khazaain, 1930, 607-608, with English translation, 4 pages.
Bancaud, "Proposal for Revised Clinical and Electroencephalographic Classification of Epileptic Seizures," Epilepsia, 22(4):489-501 (1981).
Banerjee et al., "Case Report: Aicardi syndrome: A report of five Indian cases," Neurology India, 54(1):91-93 (2006).
Barker-Haliski et al. "How Clinical Development Can, and Should Inform Translational Science," Neuron, 84:582-593 (2014).
Benowitz et al. "Metabolic and Psychophysiologic studies of cannabidiol hexobarbital interaction," Clin Pharmacol Ther., 28(1):115-120 (1980).
Bertram, "The Relevance of Kindling for Human Epilepsy," Epilepsia, 48(Suppl. 2):65-74 (2007).
Bhatt et al., "Indigenous plants in traditional healthcare system in Kedarnath valley of western Himalaya," Indian J Tradit Knowl., 7(2):300-310 (2000).
Bhattacharyya, et al. "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009).
Bipolar Health Group (Charlotte's Web Hemp Remedy, available online at http:/bipolarhealthgroup.org/index.php/charlottes-web-hemp-remedy/, accessed Sep. 6, 2017, 6 pages.
Booth, "Legalization's opening of medical pot research is dream and nightmare," Denver Post, Dec. 14, 2013, 6 pages.
Bostanci et al., "The effects of octanol on penicillin induced epileptiform activity in rats: an in vivo study," Epilepsy Research, 71:188-194 (2006).
Braida, et al., "Post-ischemic treatment with cannabidiol prevents electroencephalographic flattening, hyperlocomotion and neuronal injury in gerbils," Neuroscience Letters., 346:61-64 (2003).
Brust, J. C. M et al., "Marijuana use and the risk of new onset seizures," Trans Am Clin Climatol Assoc., 103:176-181 (1992).
Carlini et al., "Hypnotic and antiepileptic effects of cannabidiol," J Clin Pharmacol., 21:417S-427S (1981).
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
Charlotte's Web [online]. "When to Expect Results from CW Hemp Oil," Mar. 13, 2017, retrieved on May 21, 2018, https://www.cwhemp.com/blog/expecting-results-from-hemp>, 6 pages.
Charlotte's Web [online]. "Whole-Plant Cannabinoids Outperform Single Molecule Compounds," CWHemp.com, Jan. 11, 2017, retrieved on Jun. 16, 2017, <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, <http://www.childneurologyfoundation.org/disorders/lgs-lennox-gastaut-syndrome, 10 pages.
Chiron et al., "The Pharmacologic Treatment of Dravet Syndrome," Epilepsia, 52 (Suppl. 2):72-75 (2011).
Chiu et al., "The Influence of Cannabidiol and Δ-Tetrahydrocannabinol on Cobalt Epilepsy in Rats," Epilepsia, 20:365-375 (1979).
Chou, "Theoretical basis, experimental design, and computerized simulation of synergism and antagonism in drug combination studies," Pharmacol Rev., 58(3):621-681 (2006).
Conry et al., "Clobazam in the treatment of Lennox-Gastaut syndrome," Epilepsia, 50:1158-1166 (2009).
Consroe, et al., "Anticonvulsant drug antagonism of delta9tetrahydrocannabinol-induced seizures in rabbits," Res Commun Chem Pathol Pharmacol., 16(1):1-13 (1977).
Consroe, et al., "Anticonvulsant interaction of cannabidiol and ethosuximide in rats," J Pharm Pharmacol., 29(8):500-501 (1977); doi: 10.1111/j.2042-7158.1977.tb11378.x.
Consroe, et al., "Anticonvulsant nature of marijuana smoking," JAMA, 234(3):306-307 (1975).
Consroe, et al., "Cannabidiol—antiepileptic drug comparisons and interactions in experimentally induced seizures in rats," J Pharmacol Exp Ther., 201(1):26-32 (1977).
Consroe, et al., "Effects of cannabidiol on behavioral seizures caused by convulsant drugs or current in mice," Eur J Pharmacol., 83(3-4):293-298 (1982).
Consroe et al., "Chapter 2: Therapeutic Potential of Cannabinoids in Neurological Disorders," Cannabinoids as Therapeutic Agents, R. Mechoulam, Ed., 1986, pp. 21-49.
Consroe et al., Chapter 12, "Potential Role of Cannabinoids for Therapy of Neurological Disorders." p. 459 in Marijuana Cannabinoids: Neurobiology and Neurophysiology, ed. L. Murphy (1992), 72 pages.
Cortesi et al., "Potential therapeutical effects of cannabidiol in children with pharmacoresistant epilepsy," Med Hypotheses, 68(4):920-921 2007). Epub Nov. 16, 2006.
Cortez et al. Chapter 10, "Pharmacologic Models of Generalized Absence Seizures in Rodents," Models of Seizures and Epilepsy, 111-126 (2006).
Crespel et al., "Chapter 14: Lennox-Gastaut Syndrome," Chapter 14, in Epileptic Syndromes in Infancy, Childhood, and Adolescence, 5th Edition, ed., 2012, M. Bureau, et al., pp. 189-216.
Cunha, et al., "Chronic administration of cannabidiol to healthy volunteers and epileptic patients," Pharmacology, 21(3):175-85 (1980).
Czapinski, et al., "Randomized 36-month comparative study of valproic acid (VPA), phenytoin (PHT), phenobarbital (PB) and carbamazepine (CBZ) efficacy in patients with newly diagnosed epilepsy with partial complex seizures," J Neurolog Sci., 150:S162 (1997), 2 pages.
Dasa et al., "Key Attributes of TKDL: Ganja," Bhrhat Nighantu Ratnakara (Saligramanighantubhusanam), 1997, with English translation, 6 pages.
Davis, et al., "A predominant role for inhibition of the adenylate cyclase/protein kinase. A pathway in ERK activation by cannabinoid receptor 1 in NIE-115 neuroblastoma cells," J Biol Chem., 278(49):48973-80 (2003). Epub Sep. 2, 20039.
Davis, et al., "Antiepileptic action of marijuana-active substances," Federation Proceedings, 8:284-5 (1949).

(56) References Cited

OTHER PUBLICATIONS

De Meijer et al., "The inheritance of chemical phenotype in *Cannabis sativa* L. (II): Cannabigerol predominant plants," Euphytica, 145(1):189-198 (2007).
De Oliveira et al., "Anticonvulsant activity of beta-caryophyllene against pentylenetetrazol-induced seizures," Epilepsy Behav, 56:26-31 (2016).
Deshpande, et al., "Cannabinoid CB 1 receptor antagonists cause status epilepticus-like activity in the hippocampal neuronal culture model of acquired epilepsy," Neurosci Lett., 41 I(I):1-6 (2007). Epub Nov. 15, 2006.
Devinsky et al., "Cannabidiol: Pharmacology and potential therapeutic role in epilepsy and other neuropsychiatric disorders," Epilepsia, 55(6):791-802 (2014).
Dravet, "The core Dravet syndrome phenotype," Epilepsia, 52 Suppl 2:3-9 (2011); doi: 10.1111/j. 1528-1167.2011.02994. x.
Dreifus et al., "Proposal for Revised Clinical and Electroencephalographic Classification of Epileptic Seizures," Epilepsia, 22:489-501 (1981).
Dulac et al., "Use of Lamotrigine in Lennox-Gastaut and Related Epilepsy Syndromes," J. Child Neurology, 12(S1): S23-S29 (1997).
Dulac et al., "Vigabatrin in Childhood Epilepsy," J. Child Neurolog., 6(S2): S30-S37 (1991).
Eadie, "Shortcomings in the current treatment of epilepsy," Expert Rev Neurother., 12(12):1419-1427 (2012).
Eggers, "Temporal lobe epilepsy is a disease of faulty neuronal resonators rather than oscillators, and all seizures are provoked, usually by stress," Med Hypotheses.,69(6):1284-9 (2007).
Elsohly and Gul, "Constituents of Cannabis Sativa," Chapter 1, Handbook of Cannabis, Roger G. Pertwee, Ed., pp. 3-22 (2014).
Engel, "Report of the ILAE classification core group," Epilepsia, 47(9):1558-68 (2006).
Engel et al., Chapter 1. "What Should be Modeled," In Models Seizure Epilepsy, 2006, 14 pages.
Fariello, "Parenteral Penicillin in Rats: An Experimental Model of Multifocal Epilepsy," Epilepsia, 17:217-222 (1976).
FDA [Online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [Online], "Warning Letters and Test Results for Cannabidiol-Related Products," 2016 Warning Letters, retrieved on Nov. 14, 2017, URL <https://www.fda.gov/newsevents/publichealthfocus/ucm484109.htm, 4 pages.
Ferdinand, et al., "Cannabis—psychosis pathway independent of other types of psychopathology," Schizophr Res., 79(2-3):289-295 (2005).
Fisher et al., "The impact of epilepsy from the patient's perspective I. Descriptions and subjective perceptions," Epilepsy Res.,41(1):39-51 (2000).
Gabor et al., "Lorazepam versus phenobarbital: Candidates for drug of choice for treatment of status epilepticus," J Epilepsy, 3(1):3-6 (1990).
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda-approves-ind-studies-of-cbd, 4 pages.
Gastaut, "Clinical and electroencephalographical classification of epileptic seizures," Epilepsia, 11(1):102-112 (1970).
Gedde, "Clinical Experience with Cannabis in Treatment-Resistant Pediatric Epilepsy," Marijuana for Medical Professionals Conference, http://www.theroc.us/images/gedde presentation.pdf, Sep. 9-11, 2014, 45 pages.
Gedde et al., "3:330: Whole Cannabis Extract of High Concentration Cannabidiol May calm Seizures in Highly Refractory Pediatric Epilepsies," American Epilepsy Society, Dec. 2013, pp. 449-450.
Geffrey et al., "Cannabidiol (CBD) Treatment for Refractory Epilepsy in Tuberous Sclerosis Complex," American Epilepsy Society, Annual General Meeting, Abstract, accessed on Jun. 23, 2015; https://www.aesnet.org/meetings_events/annual_meeting_abstracts/view/1868979, 2 pages.
Green, "Cbd: An Unconventional Therapy," available online at http://nugs.com/article/cbd-an¬unconventional-therapy.html, published Mar. 24, 2014, 5 pages.
Gresham, et al., "Treating Lennox-Gastaut syndrome in epileptic pediatric patients with third generation rufinamide, " Neuropsychiatr Dis Treat., 6:639-645 (2010).
Gross et al., "Marijuana use and epilepsy: prevalence | patients of tertiary care epilepsy center," Neurology, 62(11):2095-2097 (2004).
Guerrini, et al., "Lamotrigine and Seizure Aggravation in Severe Myoclonic Epilepsy," Epilepsia, 39(5):508-512 (1998).
Guimares, et al., "Antianxiety effect of cannabidiol in the elevated plus-maze," Psychopharmacology (Berl)., 100(4):558-9 (1990); doi: 10.1007/BF02244012.
Heinemann et al., "An overview of in Vitro Seizure Models in Acute and Organotypic Slices," Chapter 4, pp. 35-44 (2006).
Hill, "Cannabidivarin-rich cannabis extracts are anticonvulsant in mouse and rat via a CB1 receptor-independent mechanism," British Journal of Pharmacology, 170(3):679-692 (2013).
Hill, et al., "Δ9-Tetrahydrocannabivarin suppresses in vitro epileptiform and in vivo seizure activity in adult rats." Epilepsia, 51(8):1522-32 (2010); doi: 10.1111/j.1528-1167.2010.02523. x. Epub Feb. 26, 2010.
Holmes et al., "Choosing the Correct AED: From Animal Studies to the Clinic," Pediatr Neurol, 38(3):151-162 (2008).
Iannotti, et al., "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-41 (2014); doi: 10.1021/cn5000524.
ICE Epilepsy Alliance, The Dravet Syndrome Spectrum, Nov. 2008, 2 pages.
IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.
Iuvone, et al., "Neuroprotective effect of cannabidiol, a nonpsychoactive component from Cannabis sativa, on beta-amyloid-induced toxicity in PC12 cells," J Neurochem., 89(1):134-41 (2004).
Izzo et al.; "Non-psychotropic plant cannabinoids: new therapeutic opportunities from an ancient herb," Trends | Pharmacological Sciences, 30(10):515-527 (2009).
Jacobson & Porter, "Survey of Current Cannabidiol Use in Pediatric Treatment-Resistant Epilepsy," Apr. 22, 2013; https://www.thcint.com/uploads/1/9/3/7/19371199/cannabidiol_use_in_pediatric_epilepsy.pdf, 1 page.
Jeavons, et al., "Sodium valproate in treatment of epilepsy," Br Med J., 2(5919):584-6 (1974).
Jones et al., "Cannabidiol displays antiepileptiform and antiseizure properties in vitro and in vivo," J Pharmacol Exp Ther., Feb. 2010; 332(2):569-77. doi:10.1124/jpet.109.159145. Epub Nov. 11, 2009.
Jones et al. [online], Info & Metrics / Article Information,"Cannabidiol Displays Antiepileptic from and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Joy, et al., "Marijuana and Medicine. Assessing the Science Base," National Academy Press. Washington D.C., 1999, 170 pages.
Kahan, et al., "Risk of selection bias in randomized trials," Trials, 16:405 (2015), 7 pages.
Kampa-Schittenhelm et al., Abstract. "Epigenetic hypomethylation of the 5'UTR of NADPH oxidase 4 (NOX4) by cannabidiol (CBD) results in increased protein expression, catalyzation of reactive oxygen species (ROS) and induction of apoptosisin acute leukemia," Oncol. Res. Treat., 40(Suppl 3):22 (2017), 1 page.
Kaplan, "F.D.A. Panel Recommends Approval of Cannabis-Based Drug for Epilepsy," NY Times, Apr. 19, 2018, retrieved on Jun. 20, 2018, URL <https://www .nytimes.com/2018/04/19/health/epidiolex-fda-cannabis-marajuana.html>, 3 pages.

(56) References Cited

OTHER PUBLICATIONS

Karler, et al., "The cannabinoids as potential antiepileptics," J Clin Pharmacol, 21(8-9 Suppl):437S-447S (1981).
Khan et al., "Key Attributes of TKDL: Laooq-e-Quinnab/Barai Zeequn-Nafs," Khazaain-al-Advia, 1911, (with English translation), 2 pages.
Khan et al., Key Attributes of TKDL: Nushka-e-Qutoor, Muheet-e-Azam, 1887 (with English translation), Exhibit, 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Klitgaard, et al., "Evidence for a unique profile of levetiracetam in rodent models of seizures and epilepsy," European Journal of Pharmacology, 353(2):191-206 (1998).
Klitgaard, et al., "Electrophysiological, neurochemical and regional effects of levetiracetam in the rat pilocarpine model of temporal lobe epilepsy," Seizure, 12(2):92-100 (2003).
Kramer, et al., "Febrile infection-related epilepsy syndrome (FIRES): pathogenesis, treatment, and outcome: a multicenter study on 77 children," Epilepsia, 52(11):1956-65 (2011); doi:10.1111/j.1528-1167.2011.03250. x. Epub Aug. 29, 2011.
Kuhn et al., "Potent activity of carfilzomib, a novel, irreversible inhibitor of the ubiquitin-proteasome pathway, against preclinical models of multiple myeloma," Blood, 110(9):3281-3290 (2007).
Kwan et al., "Definition of drug resistant epilepsy: consensus proposal by the ad hoc Task Force of the ILAE Commission on Therapeutic Strategies," Epilepsia, 51(6):1069-77 (2010); doi:10.1111/j. 1528-1167.2009.02397. x. Epub Nov. 3, 2009. Erratum in: Epilepsia. Sep. 2010;51(9): 1922.
Leo, et al., "Cannabidiol and epilepsy: Rationale and therapeutic potential," Pharmacological Research, 107:85-92 (2017).
Lewis, "Mystery Mechanisms," The Scientist.com, Jul. 29, 2016, retrieved on Nov. 8, 2017, 2 pages.
Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).
Lieu, et al., "Assessment of self-selection bias in a pediatric unilateral hearing loss study," Otolaryngol Head Neck Surg., 142(3):427-433 (2010).
Long, et al., "The pharmacological actions of cannabidiol," Drugs of the Future, 30(7):747-53 (2005).
Loscher and Schmidt, "Modern antiepileptic drug development has failed to deliver: ways out of the current dilemma," Epilepsia, 52(4):657-78 (2011); doi:10.1111/j.1528-1167.2011.03024. x.
Lowenstein, "Chapter 363: Seizures and Epilepsy," Diseases of the Central Nervous System, 2498-2512 (2008).
Luttjohann, et al., "A revised Racine's scale for PTZ-induced seizures in rats," Physiol Behav., 98(5):579-86 (2009); doi: 10.1016/j.physbeh.2009.09.005.
Lutz, "On-demand activation of the endocannabinoid system in the control of neuronal excitability and epileptiform seizures," Biochem Pharmacol., 68(9):1691-8 (2004).
Maa et al., "The case for medical marijuana in epilepsy," Epilepsia, 55(6):783-786 (2014).
Mackie, "Cannabinoid receptors as therapeutic targets," Annu Rev Pharmacol Toxicol., 46:101-22 (2006).
Majoosi, et al. Kaamil-al-Sena'ah, Part II, Central Council for Research in Unani Medicine. 2005: 116. Arabic. Exhibit 2, 2 pages, Translation.
Malfait, et al. "The nonpsychoactive cannabis constituent cannabidiol is an oral anti-arthritic therapeutic in murine collagen-induced arthritis," PNAS, 97(17):9561-9566 (2000).
Manni et al., "Obstructive Sleep Apnea in a Clinical Series of Adult Epilepsy Patients: Frequency and Features of the Comorbidity," Epilepsia, 44(6):836-840 (2003).
Manno, "Status Epilepticus: Current Treatment Strategies," The Neurohospitalist, 1(1):23-31 (2011).
Mares et al., "Chapter 12: Electrical Stimulation-Induced Models of Seizures," Model of Seizures and Epilepsy, Asla Pitkanen, Philip A. Schwartzkroin & Solomon L. Moshe, Eds., 2004, pp. 153-159.
Martin et al., "Structure-Anticonvulsant Activity Relationships of Cannabidiol Analogs," National Institute on Drug Abuse, Research Monograph Series, 79:48-58 (1987).
Mattson, et al., "Comparison of carbamazepine, phenobarbital, phenytoin, and primidone in partial and secondarily generalized tonic-clonic seizures," N. Engl. J. Med, 313(3):145-151 (1985).
Mattson, et al., "Prognosis for total control of complex partial and secondary generalized tonic clonic seizures," Neurology, 47:68-76 (1996).
McCormick et al., "On the cellular and network bases of epileptic seizures," Annu Rev Physiol., 63:815-846 (2001).
McNamara, "Chapter 19: Pharmacotherapy of the Epilepsies,", Goodman & Gilman's The Pharmacological Basis of Therapeutics 11th ed., McGraw-Hill Companies, pp. 501-525 (2006).
Mechoulam et al., "Cannabidiol: an overview of some pharmacological aspects," J Clin Pharmacol, 42(1 Suppl):11S-19S (2002).
Mechoulam, et al., "Toward drugs derived from cannabis," Naturwissenschaften, 65(4):174-9 (1978).
Merlis, "Proposal for an international classification of the epilepsies," Epilepsia, 1(1):114-9 (1970).
Miller, et al., "Mapping genetic modifiers of survival in a mouse model of Dravet syndrome," Genes, Brain, and Behavior, 13:163-172 (2014).
Moral, et al., "Pipeline on the Move," Drugs of the Future, 39(1):49-56 (2014).
Morard, et al., "Conversion to Sirolimus-Based Immunosuppression in Maintenance Liver Transplantation Patients," Liver Transplantation, 13:658-664 (2007).
Morelli et al., "The effects of cannabidiol and its synergism with bortezomib in multiple myeloma cell lines. A role for transient receptor potential Vanilloid type-2," Blood, 110(9):3281-3290 (2014).
MyVirtualMedicalCentre [online], "Aicardi syndrome," mymc.com, Feb. 2004, retrieved on Jan. 25, 2019 at https://www.myvmc.com/diseases/aicardi-syndrome/, 6 pages.
Nabissi et al., "Cannabinoids synergize with carfilzomib, reducing multiple myeloma cells viability and migration," Oncotarget, 7:77553 (2016), 15 pages.
Neto, et al., "The role of polar phytocomplexes on anticonvulsant effects of leaf extracts of Lippia Alba (Mill.) N.E. Brown chemotypes," J. Pharm Pharmacol. 61(7):933-9 (2009).
Ng et al., "Illicit drug use and the risk of new-onset seizures," Am J Epidemiol., 132(1):47-57 (1990).
Oakley, et al., "Dravet Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazol-induced seizures in rats," Peptides, 28(6):1214-9 (2007). Epub Apr. 19, 2007.
Pelliccia, et al., "Treatment with CBD in oily solution of drug-resistant paediatric epilepsies," Available online Sep. 2, 2010, Retrieved Jun. 30, 2015; http://www.gwpharm.com/uploads/pelliccia-2002-treatmentwithcbdinoilysolutionofdrug-resistantpediatricepilepsies.pdf, 2 pages.
Pereira, et al., "Study pharmacologic of the GABAergic and glutamatergic drugs on seizures and status epilepticus induced by pilocarpine in adult Wistar rats," Neurosci Lett., 419(3):253-7 (2007). Epub Apr. 13, 2007.
Pertwee, "Cannabinoid receptor ligands: clinical and neuropharmacological considerations, relevant to future drug discovery and development," Expert Opin Investig Drugs, 9(7):1553-71 (2000).
Pertwee et al., "The diverse CB1 and CB2 receptor pharmacology of three plant cannabinoids: delta9-tetrahydrocannabidiol, cannabidiol and delta9-tetrahydrocannabivarin," Br J Pharmacol., 153(2):199-215 (2008). Epub Sep. 10, 2007.

(56) References Cited

OTHER PUBLICATIONS

Petrocellis, et al., "Effects of cannabinoids and cannabinoid-enriched Cannabis extracts on TRP channels and endocannabinoid metabolic enzymes," British Journal of Pharmacology, 163: 1479-1494 (2011).
Pohl, et al., "Effects of flunarizine on Metrazol-induced seizures in developing rats," Epilepsy Res., 1(5):302-5 (1987).
Poortman-Van Der Meer, "A contribution to the improvement of accuracy in the quantitation of THC," Forensic Science International, Apr. 1999, 101(1):1-8.
Porter et al., "Randomized, multicenter, dose-ranging trial of retigabine for partial-onset seizures," Neurology, 68(15):1197-1204 (2007).
Porter et al., "Report of a parent survey of cannabidiol-enriched cannabis use in pediatric treatment-resistant epilepsy," Epilepsy Behavior, 29(3):574-577 (2013).
Potter, "Cannabis Horticulture," Chapter 4, Handbook of Cannabis, ed. Roger G. Pertwee, pp. 65-88 (2014).
Press, et al., "Parental reporting of response to oral cannabis extracts for treatment of refractory epilepsy." Epilepsy Behav. Apr. 2015; 45:49-52. doi: 10.1016/j.yebeh.2015.02.043. Epub Apr. 3, 2015.
Pouton, "Lipid formulations for oral administration of drugs: non-emulsifying, self-emulsifying and 'self- micro emulsifying' drug delivery systems," Eur J Pharm Sci, 11(Suppl. 2): S93-S98 (2000).
Pruitt et al., "Ethanol in Liquid Preparations Intended for Children," Pediatrics, 73(3):405-407 (1984).
Raab et al., "Multiple myeloma," Lancet, 374(9686):324-339 (2009).
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani, et al. "Epilepsy in Aicardi—Goutieres syndrome," Official J Eur Paediatric Neurology Society, 18:30-37 (2014).
Rauca, et al. "The role of superoxide dismutase and alpha-tocopherol in the development of seizures and kindling induced by pentylenetetrazol—influence of the radical scavenger alpha-phenyl-N-tert-butyl nitrone," Brain Res. May 29, 2004;1009(1-2):203-12.
Resstel et al., "5-HT1A receptors are involved in the cannabidiol-induced attenuation of behavioural and cardiovascular responses to acute restraint stress in rats," Br J Pharmacol., 156(1):181-188 (2009).
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Rubio, et al. "In vivo Experimental Models of Epilepsy," Central Nervous System Agents in Medicinal Chemistry, 10:298-309, 2010.
Russo, "Taming THC: potential cannabis synergy and phytocannabinoid-termoid entourage effects," British J. of Pharm. 1333 (2011), 21 pages.
Sadanandasarma et al., Key Attributes of TKDL: Suddha Bhanga Visista Gunah Aur Matra, Rasatarangini, 11th Ed. 1979:720-3. Sanskrit, w/English translation, 8 pages.
Sander, "The epidemiology of epilepsy revisited." Curr Opin Neural. Apr. 2003; 16(2): 165-70.
Sastri et al., "Key Attributes of TDKL: Vijaya Kalpha Apasmaranasaka," Anandakandam. 1st Edition. 1952:241. Sanskrit, 5 pages, w/English translation.
Scuderi et al., "Cannabidiol in medicine: a review of its therapeutic potential in CNS disorders," Phytother Res., 23(5):597-602 (2009).
Shukla. [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva, R. et al., "Clobazam as Add-on Therapy in Children with Epileptic Encephalopathy," Can. J. Neurol. Sci., 33:209-213 (2006).
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).

Stephenson, "In Memoriam: Professor Jean Aicardi (1926-2015)," Pediatric Neurology, Jan. 2016, 54:3-4.
Stott et al., "Cannabinoids for the pharmaceutical industry," Euphytica, 140:83-93 (2004).
Strickley, "Solubilizing Excipients in Oral and Injectable Formulations, " Table VIII, Pharmaceutical Research, 21(2):201-230 (2004).
Swann et al., "The effects of seizures on the connectivity and circuitry of the developing brain," Ment Retard Dev Disabil Res Rev. 2004; 10(2):96-100.
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thumma et al., "Influence of plasticizers on the stability and release of a prodrug of ./19-tetrahydrocannabinol incorporated in poly (ethylene oxide) matrices," Eur J Pharmaceutics and Biopharmaceutics, 70(2):605-614 (2008).
Thurman et al., "Standards for epidemiologic studies and surveillance of epilepsy," Epilepsia, 52 (Suppl 7):2-26 (2011).
Thurstone, "Avoid Charlotte's Web for Epilepsy," Jun. 26, 2014, URL <http://drthurstone.com/charlotted-web-not-safest-option-epilepsy-treatment/>, 4 pages.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia., 20:351-363 (1979).
Unimed Pharmaceuticals, Inc., "Marinol®," Jul. 2006 <https://www.accessdata.fda.gov/dmgsatfda docs/label/2006/018651 s025s026lbl.pdf>, 11 pages.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Usami et al., "Synthesis and pharmacological evaluation in mice of halogenated cannabidiol derivatives," Chem Pharm Bull (Tokyo), 47(11):1641-1645 (1999).
Utah.gov [online], "2nd Agenda Controlled Substances Advisory Committee Meeting," Nov. 12, 2013, URL <https://www.utah.gov/pmn/files/81459.pdt>, 63 pages.
Van Rijckevorsel, "Treatment of Lennox-Gastaut syndrome: overview and recent findings," Neuropsychiatr Dis Treat. Dec. 2008; 4(6): 1001-1019.
Velasco et al., "Anticancer mechanisms of cannabinoids," Curr Oncol., 23(S1):S23-S32 (2016).
Velisek, "Models of Chemically-Induced Acute Seizures," Elsevier, 2006, pp. 127-152.
Veliskova, Chapter 48 "Behavioral Characterization of Seizures in Rates," Model Seizures Epilepsy, 601-611 (2006).
Vollner et al., "Haschisch XX: Cannabidivarin, a new hashish substance, "Tetrahedron Lett. 1969;10(3):145-7.
Wahle et al., "Development of tolerance to the anticonvulsant effect of valproate but not to ethosuximide in a rat model of absence epilepsy," Eur J Pharma. May 1990;181(1-2):1-8.
Wallace et al., "Pharmacotherapy for Dravet Syndrome," Pediatr. Drugs, 18:197-208 (2016).
Weston et al., "Tetrahydrocannabivarin exhibits anticonvulsant effects in a piriform cortical brain slice model of epileptiform activity." Pro British Pharm Soc 75th Anniv Meeting. Dec. 31, 2006. Found on: http://www.pA2on1ine.org/abstract/abstract.jsp?abid=28533. Abstract Only. 1 Page.
Wingerchuk, "Cannabis for medical purposes: cultivating science, weeding out the fiction," Lancet. Jul. 24-30, 2004;364(9431):315-6.
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Metodichny Chasopis, 6(50):21-29 (2005) (with English Abstract).
Zhao et al., "Chapter 27: Repetitive Seizures in the Immature Brain," Models of Seizures and E[epilepsy, 341-350 (2006).

(56) References Cited

OTHER PUBLICATIONS

Zhornitsky & Potvin, "Cannabidiol in Humans—The Quest for Therapeutic Targets," Pharmaceuticals, 5:529-552 (2012).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).

* cited by examiner

COMBINATION OF CANNABINOIDS IN THE TREATMENT OF LEUKEMIA

RELATED APPLICATIONS

This Application is a Continuation of U.S. application Ser. No. 16/488,821, filed Aug. 26, 2019, which is a national stage filing under 35 U.S.C. 371 of International Patent Application Serial No. PCT/GB2018/050421, filed Feb. 16, 2018. The entire contents of each of these applications are incorporated herein by reference in their entirety.

FIELD OF THE INVENTION

The present invention relates to the use of a combination of two different cannabinoids in the treatment of leukaemia. The combination of CBD with THC appears to be particularly effective in reducing cell number in this disease.

Preferably the cannabinoids are used in the form of an extract of *Cannabis* such that many of the naturally occurring compounds are co-extracted with the THC or CBD. Alternatively, the cannabinoids are present in the form of a highly purified extract of *Cannabis*, wherein the CBD or THC are present at greater than 98% of the total extract (w/w) and the other components of the extract are characterised. Alternatively, the CBD and THC may be synthetically produced. A specific ratio of CBD and THC such as 10:1 to 1:10 (CBD:THC) or more preferably between 2:1 to 1:2 (CBD:THC) may be used.

In a further embodiment of the invention the CBD and THC are used in combination with a chemotherapeutic agent to treat the leukaemia. It has been found that the cannabinoid-pair CBD and THC can work synergistically with the chemotherapeutic agent vincristine or cytarabine to reduce cell number and viability. The CBD-THC pair may be formulated for administration separately, sequentially (including before and/or after), or simultaneously with one or more chemotherapeutic drugs or the combination may be provided in a single dosage form. Where the CBD+THC pair may be formulated for administration separately, sequentially or simultaneously to the chemotherapeutic agent, it may be provided as a kit or together with instructions to administer the one or more components in the manner indicated. It may also be used as the sole medication, i.e. as a monotherapy.

BACKGROUND TO THE INVENTION

Leukaemia is a group of cancers that usually begin in the bone marrow and result in high numbers of abnormal white blood cells. Symptoms include bleeding and bruising problems, feeling tired, fever, and an increased risk of infections. Symptoms occur due to a lack of normal blood cells. Diagnosis is typically made by blood tests or bone marrow biopsy.

The exact cause of leukaemia is unknown. Different kinds of leukaemia are believed to have different causes. Both inherited and environmental factors are believed to be involved. Risk factors include smoking, ionizing radiation, some chemicals (such as benzene), prior chemotherapy, and Down syndrome. People with a family history of leukaemia are also at higher risk.

There are two main types of leukaemia: lymphoblastic leukaemia and myeloid leukaemia, each type can be split into acute sub-types, such as acute lymphoblastic leukaemia (ALL) and acute myeloid leukaemia (AML), and chronic sub-types such as chronic lymphoblastic leukaemia (CLL) and chronic myeloid leukaemia (CML).

A model for lymphoblastic leukaemia is the CEM cell line which more specifically is an acute model and a model for the myeloid leukaemia is the HL60 cell line which again is an acute model.

Treatment for leukaemia often involves a combination of chemotherapy, radiation therapy, targeted therapy, and bone marrow transplant. The success of treatment depends on the type of leukaemia and the age of the person.

Leukaemia is the most common type of cancer in children, with three quarters of cases in children being the acute lymphoblastic type. However, about 90% of all leukaemias are diagnosed in adults, with AML and CLL being most common in adults.

The type of chemotherapeutic drug used to treat leukaemia often depends upon the type of disease that has been diagnosed.

In acute lymphoblastic leukaemia (ALL) the chemotherapy medicines used include: asparaginase, blinatumomab, clofarabine, daunorubicin, doxorubicin, methotrexate, nelarabine, or vincristine. Corticosteroids such as dexamethasone or prednisone are also often administered.

In acute myelogenous leukaemia (AML) the chemotherapy medicines used include: cytarabine, daunorubicin, idarubicin, or mitoxantrone.

In chronic lymphocytic leukaemia (CLL) the chemotherapy medicines bendamustine, chlorambucil, cyclophosphamide, fludarabine, or vincristine are often used, these are often used in addition to corticosteroids, such as prednisone, and monoclonal antibodies, such as alemtuzumab or rituximab.

In chronic myeloid leukaemia (CML) the chemotherapy medicines cyclophosphamide or cytarabine are commonly used in addition to tyrosine kinase inhibitors such as dasatinib, imatinib, or nilotinib There are a number of side effects associated with chemotherapeutic medications; these include nausea and vomiting, fatigue, hair loss, pain, sore mouth and throat, diarrhoea, nervous system disorders and blood disorders. These side effects can be so severe and can have such an impact on a patient's quality of life they may wish to stop treatment even though this may shorten their life.

There is growing evidence to support a role for cannabinoids in cancer therapy. Their effects in the induction of cell death, inhibition of proliferation and anti-metastatic activity in different human cancer in vitro and in vivo models have been documented (Velasco et al., 2016).

The most relevant effect of cannabinoids in cancer was investigated with tetrahydrocannabinol (THC) and cannabidiol (CBD). THC and CBD were able to reduce cell proliferation and induce autophagic-dependent cell death in glioblastoma (GBM), hepatocellular carcinoma, melanoma and breast cancer.

THC has been demonstrated to interact with existing anti-leukaemia therapies. Synergistic interactions between THC and cytarabine, doxorubicin and vincristine on the cell viability in a leukaemia cell line was shown (Liu et al., 2008).

Additionally, certain cannabinoids may act synergistically in reducing cell viability in leukaemia cell lines. Here the cannabinoids CBD, cannabigerol (CBG) and cannabigerovarin (CBGV) and their acid forms were tested alone or in some combinations (Scott et al., 2013).

A single patient study published in 2013 described a patient with acute lymphoblastic leukaemia which resulted in a decrease in blast cell count after treatment with *Can-* nabis oil. It was not known what the composition or content of the cannabinoids in the *Cannabis* oil was.

The present invention demonstrates the synergy of a combination of CBD and THC in the reduction of cell numbers in leukaemia cell lines. Furthermore, the present invention demonstrated that the cannabinoid-pair CBD and THC were further able to act synergistically to reduce cell number and cell viability in leukaemia cell lines. In particular the combination of CBD+THC with vincristine was of particular significance. This surprising result would enable a lower or sub-effective dose of the chemotherapeutic to be used.

BRIEF SUMMARY OF THE DISCLOSURE

In accordance with a first aspect of the present invention there is provided a combination of cannabidiol (CBD) and tetrahydrocannabinol (THC) for use in the treatment of leukaemia.

In one embodiment the leukaemia is lymphoblastic leukaemia. Preferably the lymphoblastic leukaemia is acute lymphoblastic leukaemia (ALL) or chronic lymphoblastic leukaemia (CLL).

In a further embodiment the leukaemia is myeloid leukaemia. Preferably the myeloid leukaemia is acute myeloid leukaemia (AML) or chronic myeloid leukaemia (CML).

In a further embodiment the leukaemia is a childhood leukaemia.

Preferably the CBD and/or THC are present in the form of at least one extract from at least one *Cannabis* plant. The *Cannabis* plant(s) preferably include at least one *Cannabis* chemovar. Most preferably the plant extract will be a botanical drug substance (BDS), as defined herein.

The CBD and/or the THC may be present as a highly purified extract of *Cannabis* which comprises at least 98% (w/w) of the particular cannabinoid. Alternatively, the CBD and/or the THC are present as a synthetic compound.

The CBD and THC are preferably present in a ratio of from 10:1 to 1:10 (CBD:THC). More preferably the CBD and THC are present in a ratio of from 5:1 to 1:5 (CBD:THC), through 2:1 to 1:2 (CBD:THC), 1.08:1 to 1:1.08 (CBD:THC) to approximately 1:1 (CBD:THC).

The CBD and THC are preferably present in a combined dose of from 0.1 to 100 mg/kg/day. In certain circumstances where greater doses of cannabinoids are required the amount of cannabinoid present are in a dose of 0.1 to 100 mg/kg/day per cannabinoid.

In a further embodiment of the present invention the combination of CBD and THC further comprises a chemotherapeutic drug.

Preferably the chemotherapeutic drug is: cytarabine or vincristine.

Preferably where the chemotherapeutic drug is vincristine the type of leukaemia to be treated is lymphoblastic leukaemia.

Alternatively, where the chemotherapeutic drug is cytarabine the type of leukaemia to be treated is myeloid leukaemia.

Preferably the CBD and THC are administered separately, sequentially or simultaneously to the chemotherapeutic drug.

Preferably the CBD and THC are administered sequentially before the chemotherapeutic drug. Alternatively, the CBD and THC are administered sequentially after the chemotherapeutic drug. Indeed, the CBD and THC may be administered sequentially before and after the chemotherapeutic drug.

The dose of chemotherapeutic drug may be provided at sub-effective or sub-optimal levels in order to reduce the side effects associated with chemotherapeutic agents.

Preferably the dose of chemotherapeutic drug is reduced by at least 20% of the therapeutically effective dose when used alone, more preferably the dose is reduced by at least 50% of the therapeutically effective dose when used alone. Where the cannabinoids are able to work in a statistically significant manner the dose of chemotherapeutic drug may even be reduced by at least 100% or even at least 200% or more of the therapeutically effective dose when used alone.

Preferably, the CBD and THC which may further comprise a chemotherapeutic drug is formulated as a pharmaceutical composition further comprising one or more pharmaceutically acceptable carriers, excipients or diluents. The composition may be formulated into pharmaceutical dosage forms which may contain other pharmaceutically acceptable excipients for modifying conditions such as pH, osmolarity, taste, viscosity, sterility, lipophilicity, solubility etc. The choice of diluents, carriers or excipients will depend on the desired dosage form, which may in turn be dependent on the intended route of administration to a patient.

In accordance with a second aspect of the present invention there is provided a method of treating leukaemia comprising administering cannabidiol (CBD) and tetrahydrocannabinol (THC) to a subject in need thereof. Preferably the subject is a human.

Preferably the method of treatment further comprises a chemotherapeutic drug, particularly vincristine or cytarabine. More preferably the CBD and THC are administered separately, sequentially or simultaneously to the chemotherapeutic drug.

DEFINITIONS

Definitions of some of the terms used to describe the invention are detailed below:

The cannabinoids described in the present application are listed below along with their standard abbreviations.

TABLE 1

| Cannabinoids and their abbreviations | | |
| --- | --- | --- |
| CBD | Cannabidiol | 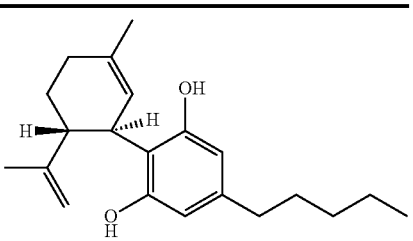 |
| THC | Tetrahydrocannabinol | 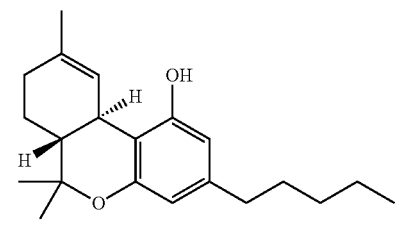 [SMILES: CCCCCc1cc(O)c2c(c1)OC(C)(C)[C@@H]1CCC(C)=C[C@@H]21] |

TABLE 1-continued

Cannabinoids and their abbreviations

| CBG | Canna-bigerol |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *Cannabis* plant. The phytocannabinoids can be isolated from plants to produce a highly purified extract or can be reproduced synthetically.

A "plant extract" is an extract from a plant material as defined in the Guidance for Industry Botanical Drug Products Draft Guidance, August 2000, US Department of Health and Human Services, Food and Drug Administration Centre for Drug Evaluation and Research.

In the context of this application the terms "*Cannabis* extract" or "extract from a *Cannabis* plant", which are used interchangeably, encompass "Botanical Drug Substances" derived from *Cannabis* plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of *Cannabis*, "botanical drug substances" derived from *Cannabis* plants do not include highly purified, Pharmacopoeial grade cannabinoids.

"Botanical drug substances" derived from *Cannabis* plants include primary extracts prepared by such processes as, for example, maceration, percolation, extraction with solvents such as C1 to C5 alcohols (e.g. ethanol), Norflurane (HFA134a), HFA227 and liquid carbon dioxide under sub-critical or super-critical conditions. The primary extract may be further purified for example by super-critical or sub-critical solvent extraction, vaporisation or chromatography. When solvents such as those listed above are used, the resultant extract contains non-specific lipid soluble material. This can be removed by a variety of processes including "winterisation", which involves chilling to −20° C. followed by filtration to remove waxy ballast, extraction with liquid carbon dioxide and by distillation.

In embodiments wherein, the cannabinoids are provided as a BDS, the BDS is preferably obtained by $CO_2$ extraction, under sub-critical or super-critical conditions, followed by a secondary extraction, e.g. an ethanolic precipitation, to remove a substantial proportion of waxes and other ballast. This is because the ballast includes wax esters and glycerides, unsaturated fatty acid residues, terpenes, carotenes, and flavonoids which are not very soluble in the chosen solvent/co-solvent, particularly the preferred co-solvent, propylene glycol, and will precipitate out. Most preferably the BDS is produced by a process comprising decarboxylation, extraction with liquid carbon dioxide and then a further extraction to remove significant amounts of ballast. Most preferably the ballast is substantially removed by an ethanolic precipitation.

Most preferably, *Cannabis* plant material is heated to a defined temperature for a defined period of time in order to decarboxylate cannabinoid acids to free cannabinoids prior to extraction of the BDS.

Botanical drug substances are formulated into "Botanical Drug Products" which are defined in the Guidance for Industry Botanical Drug Products Draft Guidance, August 2000, US Department of Health and Human Services, Food and Drug Administration Centre for Drug Evaluation and Research as: "A botanical product that is intended for use as a drug; a drug product that is prepared from a botanical drug substance."

"*Cannabis* plants" includes wild type *Cannabis sativa* and variants thereof, including *Cannabis* chemovars which naturally contain different amounts of the individual cannabinoids.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

A typical extract of *Cannabis* is Sativex, this medication may contain in a 1 ml vol: THC 25-50 mg/ml, preferably 27 mg/ml (based on amount of cannabinoid in a botanical drug substance), CBD 25-50 mg/ml, preferably 25 mg/ml (based on amount of cannabinoid in a botanical drug substance), propylene glycol 0.5 ml/ml, peppermint oil 0.0005 ml/ml, and ethanol (anhydrous) qs to 1 ml.

"Highly purified cannabinoid extracts" are defined as cannabinoids that have been extracted from the *Cannabis* plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

The therapeutically effective dose of vincristine ranges from 0.4 to 1.4 mg/m². The standard dose of vincristine used to treat leukaemia is 1.4 mg/m² administered by IV once per week.

The therapeutically effective dose of cytarabine ranges from 100 to 200 mg/m². The standard dose of cytarabine used to treat leukaemia is 100 mg/m² administered by continuous IV over 24 hours, once per fortnight.

To express a mg/m² dose as the equivalent mg/kg. dose, divide the dose by the appropriate km factor. In adult humans where the km factor is 37 the calculation for 100 mg/m$^2$ would be: 100 mg/m$^2$/37=2.7 mg/kg A "sub-optimal" or "sub-effective" dose of chemotherapeutic drug refers to a lower dose than the therapeutically effective dose.

BRIEF DESCRIPTION OF THE DRAWINGS

Embodiments of the invention are further described hereinafter with reference to the accompanying drawings, in which.

LEGENDS TO THE FIGURES

Figure 1:
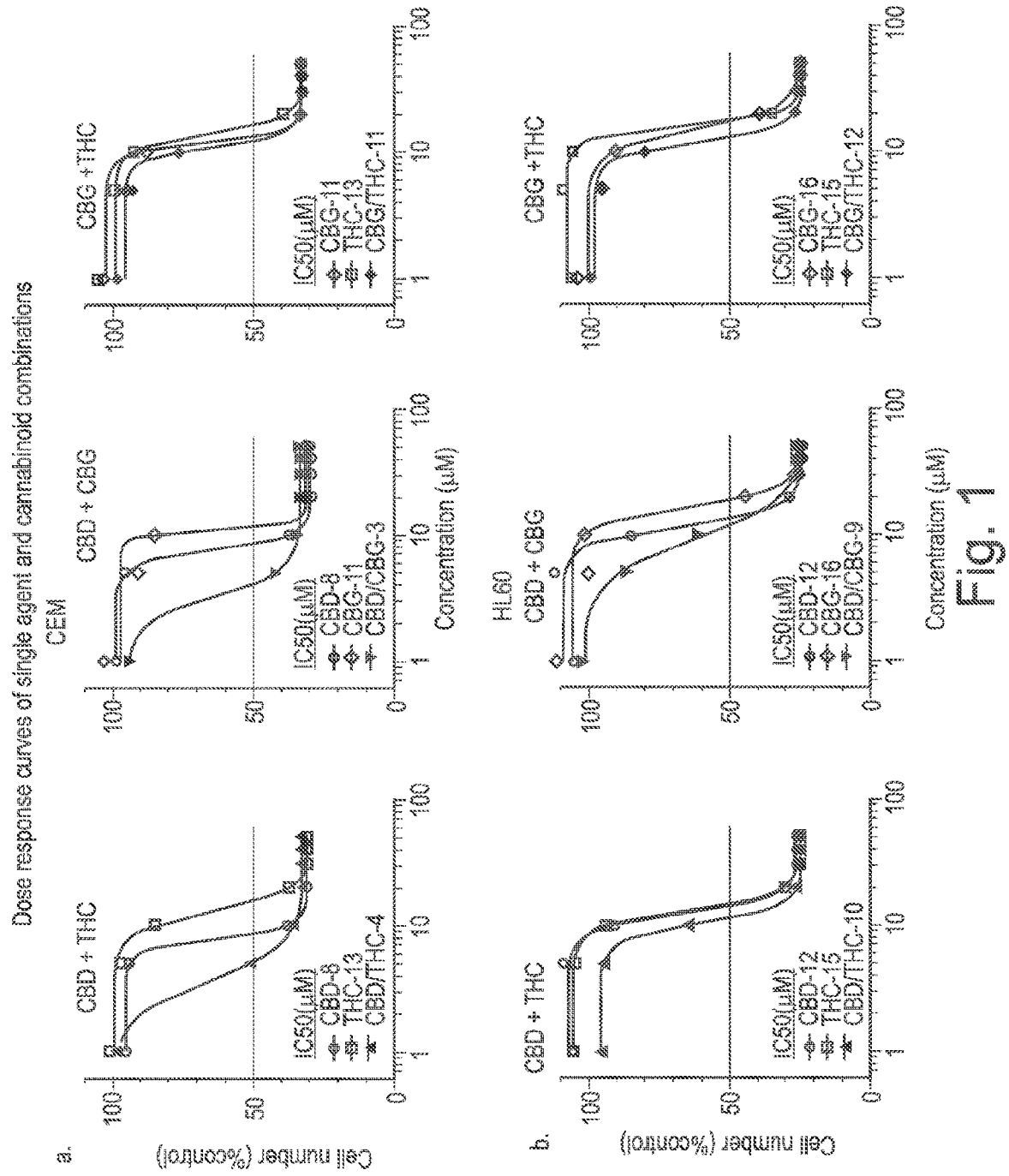
FIG. 1 shows the dose response curves of single agent and cannabinoid combinations.

FIG. 1. Dose response curves of single agent and cannabinoid combinations. CEM and HL60 cells were grown for 48 hr in the presence of increasing concentrations of the three cannabinoids, THC, CBD and CBG, either as single agents or in dual combinations prepared at a 1:1 ratio. Thus 10 μM of the CBD and THC combination would be made of 5 μM CBD+5 μM THC. Cell number was assessed using the MTT assay and the concentration required to reduce the cell number by 50% (IC50) for each condition in CEM (a) and HL60 (b) was calculated using GraphPad Prism. Each data point represents the mean of at least three separate experiments. SDs have been omitted for clarity.

Figure 2:
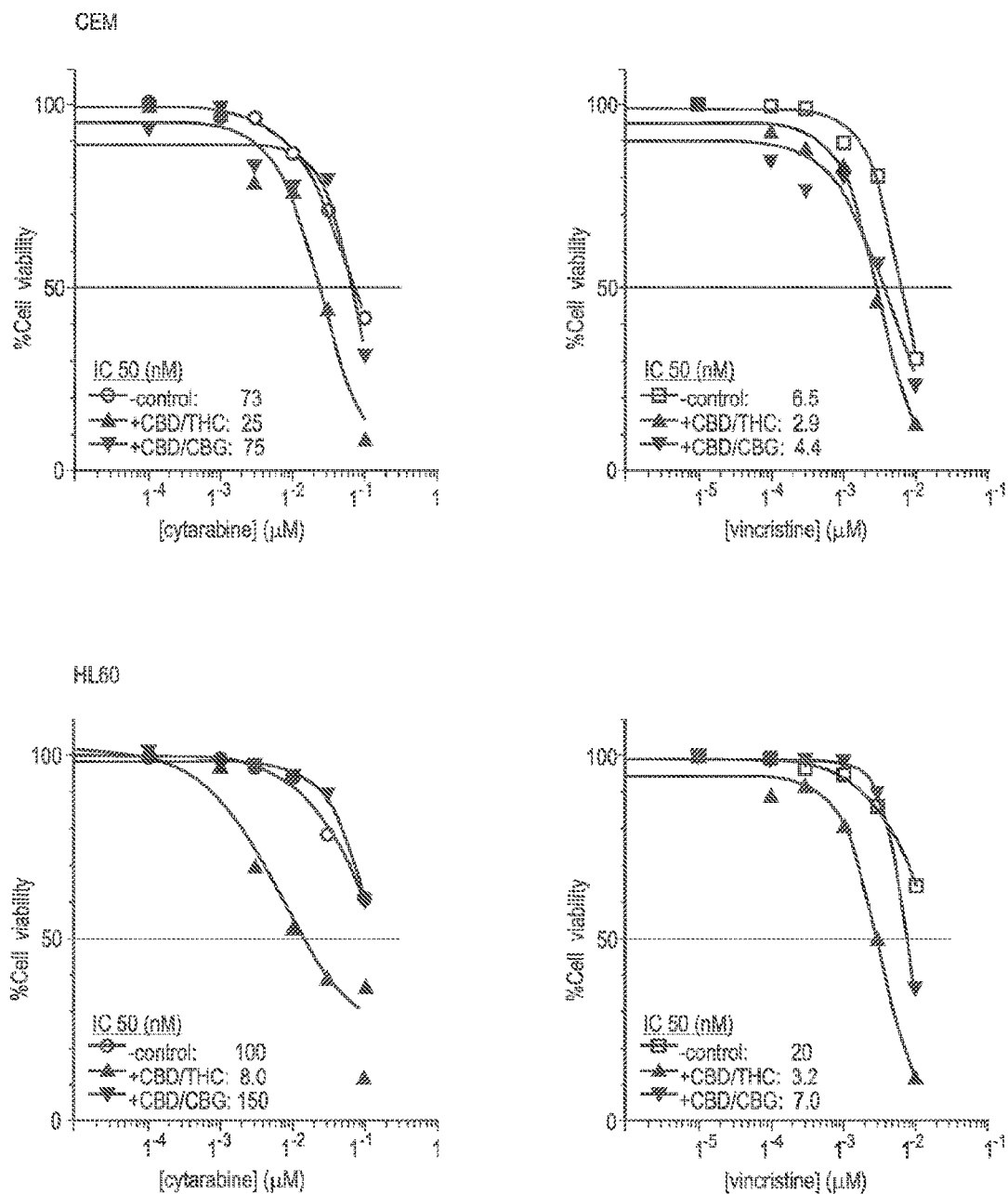
FIG. 2 shows the effect of low doses of cannabinoids in sensitising chemotherapy treatment.

FIG. 2. Sensitising chemotherapy action with low doses of cannabinoids. CEM and HL60 cells were grown for 72 hr in the presence of increasing concentrations of cytarabine (CYT) or vincristine (VIN). The effect of a low dose of CBD/THC or CBD/CBG on the activity of CYT and VIN was also assessed. IC50 values for percentage cell viability were determined by emax models.

Figure 3:
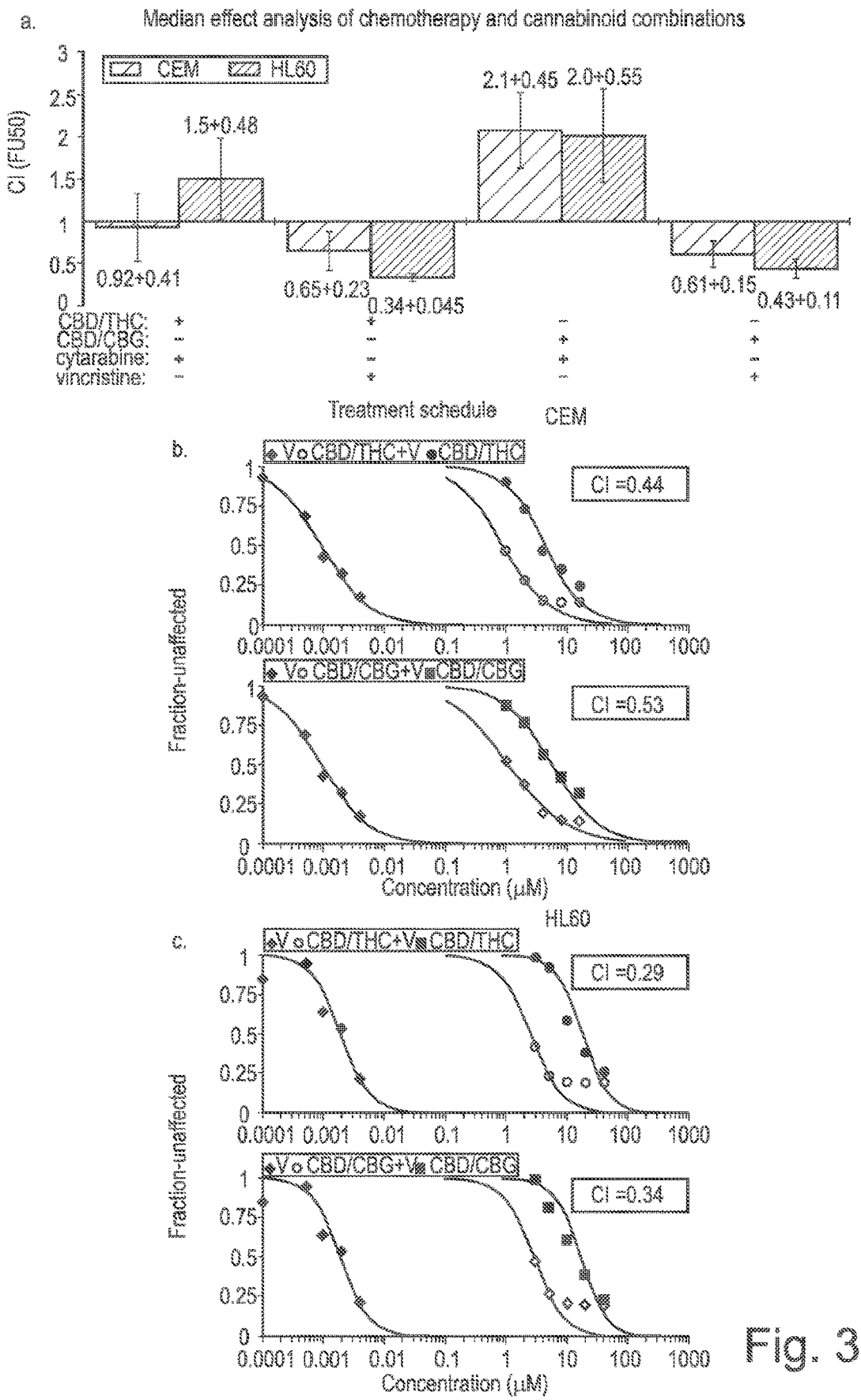
FIG. 3 shows the median effect analysis of chemotherapy and cannabinoid combinations.

FIG. 3. Median effect analysis of chemotherapy and cannabinoid combinations. CEM and HL60 cells were grown for 72 hr in the presence of increasing concentrations of both cytarabine or vincristine and a cannabinoid-pair, combined at fractions of their respective IC50s. CBD/THC and CBD/CBG were the two cannabinoid-pairs that were investigated, and were used at equal 1:1 ratios. Cell number was assessed at 72 hr using the MTT assay and defined algorithms were then used to generate a combination index score (CI) which indicates the nature of the combination interactions (CI=1=additivity; CI<1=synergy: CI>1=antagonism) (a). Representative data have also been included from experiments in CEM (b) and HL60 (c) for the cannabinoid-pairs with vincristine. Each data point in the column graph represents the mean and SD of at least three separate experiments.

Figure 4:
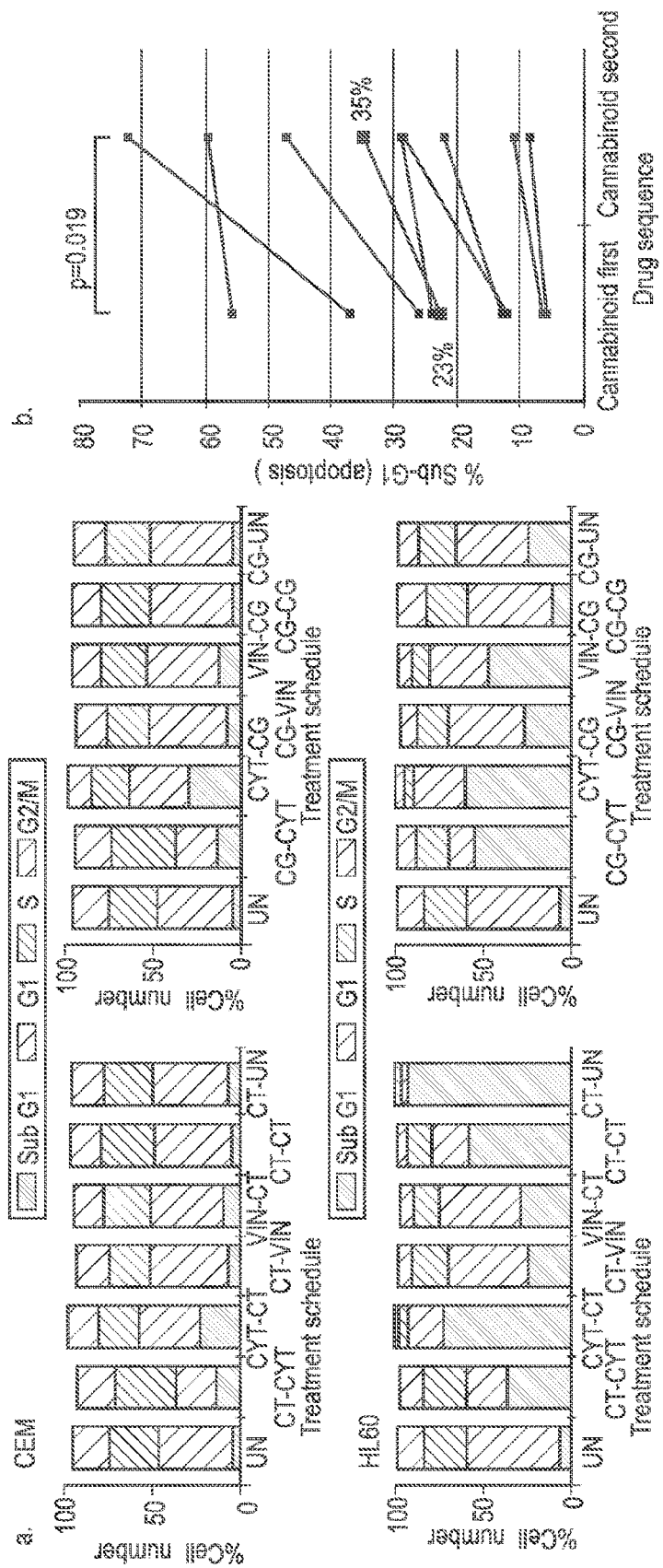
FIG. 4 shows the effect of drug sequence on the cell cycle.

FIG. 4. Effect of drug sequence on the cell cycle. CEM and HL60 cells were cultured according to schedules consisting two distinct treatment stages lasting 48 hr each. Treatments consisted of a cannabinoid—CBD+THC (CT) or CBD+CBG (CG) in the first stage, followed by cytarabine (CYT) or vincristine (VIN) in the second. Parallel cultures were also performed in which the sequence of drugs was reversed. Cell cycle distribution was then assessed by flow cytometry at 96 hr (a). The specific effect on % sub-G1 cells where a cannabinoid was used first was compared with those in which a cannabinoid was used second (b).

DETAILED DESCRIPTION

The following examples demonstrate the effects of combinations of cannabinoids on leukaemia cells lines and also the effects of cannabinoid-pairs in combination with chemotherapeutic drugs used in the treatment of leukaemia.

Synergistic effects are calculated using combination interactions (CI), where a CI equal to 1 indicates an additive effect, a CI of less than 1 demonstrates synergistic interactions of compounds and a CI of greater than 1 indicates that the two compounds are working antagonistically. Where compounds are shown to work synergistically there is a suggestion that such a combination will produce beneficial effects in use.

Such beneficial effects include a lower or sub-optimal dose of the compounds being required to produce the same effect were only one of the compounds used. This is of benefit particularly where one or more of the compounds produce side effects meaning that at lower dose side effects are reduced or removed. Further benefits that occur are that the effect produced is larger, for example the combination may produce a greater reduction in cell viability which is of particular benefit in the treatment of a cancer.

Conversely if the CI value is indicative of an antagonistic effect it would be unwise to combine the two compounds for use in the treatment of a disease, particularly a disease such as cancer. When compounds work antagonistically they can cancel the effects of each other out, thereby reducing the effectiveness of each compound. Clearly this is not a useful treatment option.

The section below describes the general methodology used in the four Examples.

General Materials and Methodology

Cell Culture and Drugs

The human cancer cell lines CEM (acute lymphocytic leukaemia) and HL60 (promyelocytic leukaemia) used (European Collection of Authenticated Cell Cultures, Salisbury, UK), and grown in RPMI-1640 medium (Sigma-Aldrich Company Ltd., Dorset, UK) supplemented with 10% foetal bovine serum (FBS) and 2 mM L-glutamine. All cell lines were incubated in a humidified atmosphere with 5% CO2 in air at 37° C., and discarded after ~12 passages.

Cytarabine (CYT), (Sigma) and vincristine (VIN), (Sigma) were reconstituted in PBS at a stock concentration of 10 mM, and kept at −20° C. for no more than four weeks.

Cannabidiol (CBD), cannabigerol (CBG) and tetrahydrocannabinol (THC) were dissolved in ethanol to appropriate concentrations that ensured a final ethanol concentration in cell cultures<0.1%.

For experiments with cannabinoids, the amount of FBS in the cell culture medium was reduced to 5%.

One aim of the current study was to investigate the benefit of using two different cannabinoids in combination. Cannabinoids were paired concomitantly at a 1:1 ratio, where the stated concentration for them reflected an equal amount of each cannabinoid-component; for example, 10 μM CBD+THC contained 5 μM CBD and 5 μM THC.

Proliferation Assays—Cannabinoids Alone

To study the effect of the cannabinoids on cell growth, leukaemia cells that were growing exponentially were seeded into 96-well plates at a density of 1.5×10$^4$/well.

Cannabinoids were then added to the wells at various concentrations, ensuring an equal volume of 200 µl across the plate.

Single-agent testing: Either CBD, CBG or THC alone was added to the wells at a concentration range of 1-50 µM.

Paired-cannabinoid testing CBD+CBG, CBD+THC or CBG+THC were added to the wells at a concentration range for the paired cannabinoids of 1-50 µM. The molarity was based upon the total cannabinoids in each pair.

Cell number was assessed after 48 h using a methylthiazoletetrazolium (MTT)-based assay.

Combination Studies—Median-Effect Analysis

Cells ($1.5 \times 10^4$/well) growing exponentially were reset in fresh culture medium and aliquoted into 96-well plates. A cannabinoid-pair (either CBD+THC or CBD+CBG) was combined with CYT or VIN at concentrations that were equal ratios of their respective IC50.

Cell number was then assessed after 72 h by the MTT-based assay, and a combination index (CI) calculated by using the median-effect equation.

Combination Studies—Modulatory Effect

The ability of cannabinoids to modify the efficacy CYT and VIN was studied by assessing and comparing the IC50 of the anti-leukaemia drugs in the absence and presence of the cannabinoids.

The cannabinoids tested were CBD+CBG and CBD+THC, and these were used at a single total sub-optimal concentration of 1 µM in CEM and 5 µM HL60.

Methodologically, cells ($5 \times 10^4$/well) growing exponentially were reset in fresh culture medium and aliquoted into 96-well plates. Drugs were added (CYT and VIN over a range of concentrations) and cell number determined after 72 h.

Parallel 6-well plates containing cells were also prepared and were cultured with the same treatment combinations described. These allowed for determination of cell cycle distribution at 72 h by flow cytometry utilising the nucleic acid stain propidium iodide.

Combination Studies—Drug Sequence and the Impact of a Recovery Phase

CEM and HL60 cells were seeded into 6-well plates at a density of $1 \times 10^6$/well and then treated according to a culture schedule that lasted a total of 96 h.

The treatment would involve two separate phases; each lasting 48 h. One set of drugs would be administered in the first 48 h phase and a second set of drugs in the following 48 h phase. The culture medium would be removed by centrifugation after the first treatment to be replaced with fresh medium in an attempt to remove the drugs used in the first phase of treatment. The drugs studied were either: CBD+CBG (4 µM in CEM and 10 µM in HL60), CBD+THC (4 µM in CEM and 10 µM in HL60), CYT (10 nM), or VIN (0.1 nM).

The effect of a recovery phase was assessed by keeping the second 48 h phase of treatment drug-free. Flow cytometry using propidium iodide staining was performed at the end of the experiment to assess the extent of cell death/apoptosis.

Immunoblotting Analysis

Western blot analyses were performed. Primary antibody probing was performed with anti-cyclin B1 and anti-GAPDH (New England Biolabs, Hitchin, UK) and used at a dilution of 1:1.000.

Appropriate HRP-conjugated secondary antibodies were then used (New England Biolabs), and bands were visualised by the ECL-plus detection system (Amersham Biosciences Ltd., Little Chalfont, UK).

Statistical Analysis

All statistical analyses were performed using GraphPad Prism or Microsoft Excel, and differences between treatments and control groups were determined by analysis of variance and subsequently by paired tests. Data values were presented as the means and SDs of at least three separate experiments.

EXAMPLE 1: EFFICACY OF COMBINATIONS OF CANNABINOIDS IN TWO LEUKAEMIA CELL LINES

This example paired CBD, CBG and THC in different permutations, and assessed their effects on cell numbers in two different cell lines after 48 h of treatment.

IC50 values for the individual cannabinoids were determined, and these were compared with the IC50 achieved when the matching cannabinoid-pair were used. Data from these experiments are shown in FIG. 1a (CEM cell line) and FIG. 1b (HL60 cell line).

In the CEM cell line CBD alone had an IC50 of 7.8 t 0.21 µM and THC alone had an IC50 of 13±0.49 µM. When CBD and THC were combined at a ratio of 1:1 an IC50 of 3.6±0.19 µM was obtained. A reduction of the IC50 by half, in the case of CBD, and two thirds in the case of THC was surprising. It would not be expected that a sub-optimal concentration of both compounds could produce the same reduction in cell number, thereby demonstrating a synergistic effect.

The combination of CBD with THC provided a greater reduction in cell number than the other combinations of CBD with CBG or THC with CBG. Furthermore, the CEM cell line appeared to be more responsive to treatments with the cannabinoids.

EXAMPLE 2: ABILITY OF CANNABINOID-PAIRS TO SENSITISE LEUKAEMIA CELL LINES TO THE EFFECTS OF CHEMOTHERAPEUTIC AGENTS

This experiment was designed to test the ability of a cannabinoid-pair to sensitise cells to the effects of CYT or VIN. The results of these are demonstrated in FIG. 2.

The ability of a sub-effective concentration of cannabinoid to alter the efficacy of CYT or VIN was determined by comparing the IC50s of the chemotherapy agents in the absence or presence of the cannabinoid-pair.

FIG. 2 demonstrates that the cannabinoid-pair CBD+THC were able to modulate the chemotherapeutics ability to reduce cell viability. For example, in the HL60 cell line the IC50 for cytarabine was 100 nM; however, this was significantly reduced to 8 nM if CBD+THC were added in combination to the chemotherapeutic. However, the addition of CBD+CBG appeared to be antagonistic as the IC50 of cytarabine increased to 150 nm when this cannabinoid-pair was used in combination.

Similar data were produced when the cannabinoid-pair CBD+THC were provided in combinations with vincristine, where a synergistic interaction led to reduced cell viability.

EXAMPLE 3: EFFICACY OF COMBINATIONS OF CANNABINOID-PAIRS WITH CHEMOTHERAPEUTIC AGENTS IN TWO LEUKAEMIA CELL LINES

Median-effect analyses were employed to assess the interactions between each cannabinoid-pairs and two chemotherapeutic drugs commonly used in the treatment of leukaemia, vincristine (VIN) and cytarabine (CYT).

Cannabinoid-pairs, CBD+CBG and CBD+THC, were combined with either CYT or VIN. CI-values were then calculated by using these results and used as a way of understanding the drug-interactions (Chou, 2006). FIGS. 3a to c detail the data produced.

The combination of the cannabinoid-pair CBD+THC with vincristine produced CI values of less than 1 in both the CEM and HL60 cell lines, suggesting that this combination is synergistic.

Combinations of the cannabinoid-pair CBD+THC with cytarabine however did not appear to be synergistic, moreover the cannabinoid-pair CBD+CBG with cytarabine appeared to be antagonistic as is shown in FIG. 3a.

These data show that in when particular combinations are used, an equivalent level of action can be obtained even though the concentrations of the agents used are much lower. For example, the cannabinoid-pair CBD+THC when used in combination with VIN produced a synergistic response when used at sub-effective levels of ~2.5 µM and ~0.25 nM, respectively.

EXAMPLE 4: SEQUENTIAL ADMINISTRATION OF CANNABINOID-PAIRS AND CHEMOTHERAPEUTIC AGENTS

Having seen synergistic interactions between cannabinoid-pairs and chemotherapeutic, when they were administered simultaneously, the impact of using the drugs sequentially was assessed.

Cells were cultured according to schedules that consisted of two rounds of treatment, each lasting 48 hrs. Each round of treatment was separated by a washing step to remove drug from the medium.

The order in which the drugs were administered was swapped in equivalent experiments to assess the counter-order of drugs. In some cases, a treatment schedule could involve the use of a cannabinoid-pair in the first round of treatment followed by no treatment in the second. This mimicked a "recovery" schedule.

Results showed that, generally, the percentage of cells within the sub-G1 population of the cell cycle were low in CEM cells following any treatments (FIG. 4a); however, the order of administration of the drugs affected the number of cells in sub-G1.

Typically, using the chemotherapeutic agent prior to administration of the cannabinoid-pair resulted in a greater number of cells in sub-G1 compared to schedules in which the order of drugs was reversed (FIG. 4a).

In HL60 cells, % sub-G1 was 37% if CBD+THC was used before CYT, but 72% if CBD+THC was used after CYT.

Furthermore, paired t-test of all the data, irrespective of cell line and drug used, showed that significantly more apoptosis was seen if the order of treatment entailed a cannabinoid-pair after a chemotherapy drug (FIG. 4b).

CONCLUSIONS

These data represented in Examples 1 to 4 and FIGS. 1 to 4 demonstrate that the combination of cannabinoids, particularly the combination of CBD with THC were able to synergistically act to reduce the cell numbers in a leukaemia cell line.

Furthermore, these data additionally demonstrate that when the cannabinoid-pairs CBD+THC are used in combination with vincristine or cytarabine a synergistic reduction in cell number and cell viability occurs. In particular the combination of CBD+THC with vincristine appeared to produce the most significant synergistic effect.

Example 4 also suggests that the cannabinoid-pair and the chemotherapeutic drug did not need to be administered at the same time to produce an effect. It was seen that administration of the cannabinoid-pair after the chemotherapeutic treatment resulted in an increase of cells undergoing apoptosis in comparison to when the cannabinoid-pair were administered prior to the chemotherapeutic drug. Such data might provide a useful indicator that in the clinical setting, where it may be difficult to administer the drugs concurrently, the administration of either the cannabinoid-pair prior to or after the treatment with the chemotherapeutic drug would provide just as good if not better results. Furthermore, priming a patient with a small dose of cannabinoid-pair before treatment with the chemotherapeutic drug, followed by the main dose of cannabinoid-pair may prove even more beneficial.

In conclusion, these data demonstrate that the combination of CBD with THC with the anti-leukaemia chemotherapeutic agents vincristine or cytarabine are effective in reducing both the cell viability of leukaemia cells. The use of such a combination may prove to be of particular clinical benefit as it would produce a better clinical outcome or reduce the amount of chemotherapeutic agent provided without a loss of activity meaning a reduction in the side effects suffered.

REFERENCES

Chou T C. Theoretical basis, experimental design, and computerized simulation of synergism and antagonism in drug combination studies. Pharmacol Rev. 2006; 58(3): 621-81.

Liu W M, Scott K A, Shamash J, Joel S and Powles TB. Enhancing the in vitro cytotoxic activity of delta-9-tetrahydrocannabinol in leukemic cells through a combinational approach. Leukemia and Lymphoma, September 2008, 49(9): 1800-1809.

Scott K A, Shah S, Dalgleish A G, Liu W M. Enhancing the Activity of Cannabidiol and Other Cannabinoids In Vitro Through Modifications to Drug Combinations and Treatment Schedules. Anticancer Research. October 2013, vol. 33, no. 10, 4373-4380

Velasco G, Sánchez C, Guzmán M. Anticancer mechanisms of cannabinoids. Curr Oncol. 2016; 23(2):S23-32.

The invention claimed is:

1. A method of treating leukemia comprising administering (i) cannabidiol (CBD) and tetrahydrocannabinol (THC), wherein CBD and THC are administered in a ratio of from 2:1 to 1:2 CBD:THC and (ii) a chemotherapeutic drug to a subject in need thereof, wherein the leukemia is acute lymphoblastic leukemia (ALL) or acute myeloid leukemia (AML).

2. The method of treating leukemia according to claim 1, wherein the CBD and the chemotherapeutic drug are administered separately.

3. The method of treating leukemia according to claim 1, wherein the leukemia is acute lymphoblastic leukemia (ALL).

4. The method of treating leukemia according to claim 1, wherein the leukemia is acute myeloid leukemia (AML).

5. The method of treating leukemia according to claim 1, wherein the leukemia is a childhood leukemia.

6. The method of treating leukaemia according to claim 1, wherein the CBD is present in the form of a *Cannabis* plant extract.

7. The method of treating leukaemia according to claim 6, wherein the CBD is present as a highly purified extract of *Cannabis* which comprises at least 98% (w/w) of CBD.

8. The method of treating leukaemia according to claim 1, wherein the CBD is present as a synthetic compound.

9. The method of treating leukemia according to claim 1, comprising administering CBD in a dose of from 0.1 to 100 mg/kg/day.

10. The method of treating leukemia according to claim 1, wherein the chemotherapeutic drug is cytarabine.

11. The method of treating leukemia according to claim 10, wherein the chemotherapeutic drug is vincristine and leukemia is acute lymphoblastic leukemia.

12. The method of treating leukemia according to claim 10, wherein the chemotherapeutic drug is cytarabine and the type of leukemia is acute myeloid leukemia.

13. The method of treating leukemia according to claim 2, comprising administering the CBD and the chemotherapeutic drug sequentially.

14. The method of treating leukemia according to claim 2, comprising administering the CBD and the chemotherapeutic drug simultaneously.

15. The method of treating leukemia according to claim 1, comprising administering CBD and THC in a ratio of 1:1 CBD:THC.

16. The method of treating leukemia according to claim 1, wherein the chemotherapeutic drug is vincristine.

* * * * *